United States Patent
Liu

(10) Patent No.: US 11,517,231 B2
(45) Date of Patent: Dec. 6, 2022

(54) BLOOD GLUCOSE TEST STRIP AND ASSOCIATED MEASURING METHOD

(71) Applicant: eMemory Technology Inc., Hsin-Chu (TW)

(72) Inventor: Hsin-Chou Liu, Hsinchu County (TW)

(73) Assignee: EMEMORY TECHNOLOGY INC., Hsin-Chu (TW)

( * ) Notice: Subject to any disclaimer, the term of this patent is extended or adjusted under 35 U.S.C. 154(b) by 440 days.

(21) Appl. No.: 16/708,494

(22) Filed: Dec. 10, 2019

(65) Prior Publication Data

US 2020/0221987 A1    Jul. 16, 2020

Related U.S. Application Data

(60) Provisional application No. 62/791,870, filed on Jan. 13, 2019.

(30) Foreign Application Priority Data

Nov. 7, 2019 (TW) .................... 108140518

(51) Int. Cl.
| | |
|---|---|
| *A61B 5/145* | (2006.01) |
| *A61B 5/15* | (2006.01) |
| *A61B 5/00* | (2006.01) |
| *G01N 27/327* | (2006.01) |
| *A61B 5/1486* | (2006.01) |

(52) U.S. Cl.
CPC ........ *A61B 5/150358* (2013.01); *A61B 5/002* (2013.01); *A61B 5/1486* (2013.01); *A61B 5/14532* (2013.01); *A61B 5/150022* (2013.01); *G01N 27/3274* (2013.01); *A61B 2560/0223* (2013.01); *A61B 2560/0475* (2013.01); *A61B 2562/0295* (2013.01)

(58) Field of Classification Search
CPC ......... G01N 27/3274; G01N 33/48771; G01N 33/96; A61B 5/15; A61B 5/145; A61B 5/150358; A61B 5/14532; A61B 5/150022; A61B 5/002; A61B 2560/0223; A61B 2562/0295; A61B 2560/0475
See application file for complete search history.

(56) References Cited

U.S. PATENT DOCUMENTS

| | | | | |
|---|---|---|---|---|
| 9,470,673 | B2* | 10/2016 | Samsoondar | B01L 3/502 |
| 9,897,610 | B2* | 2/2018 | Lipman | A61B 5/1495 |
| 2009/0148875 | A1* | 6/2009 | Lin | G01N 33/96 |
| | | | | 435/14 |
| 2013/0306493 | A1* | 11/2013 | Chatelier | C12Q 1/006 |
| | | | | 205/782 |
| 2015/0330926 | A1* | 11/2015 | Elder | G01N 27/3273 |
| | | | | 702/19 |

* cited by examiner

*Primary Examiner* — Eric J Messersmith
(74) *Attorney, Agent, or Firm* — WPAT, PC

(57) ABSTRACT

A blood glucose test strip includes a base substrate, a calibration site, a test site and a non-volatile memory. The calibration site is disposed on the base substrate. A chemical reagent is applied on the calibration site. The test site is disposed on the base substrate. A chemical reagent is applied on the test site. The non-volatile memory is disposed on the base substrate. A calibration parameter is stored in the non-volatile memory. During a calibrating procedure, the calibration solution is dropped on the calibration site, a calibration parameter is calculated according to a first reaction result of the calibration solution and the chemical reagent, and the calibration parameter is stored in the non-volatile memory.

13 Claims, 2 Drawing Sheets

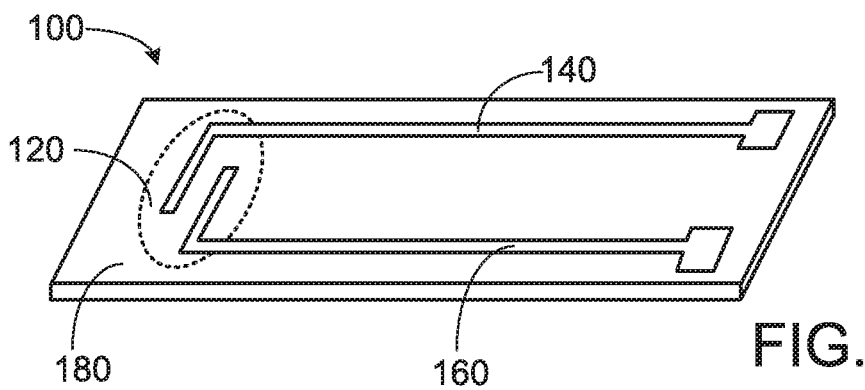

FIG. 1 (PRIOR ART)

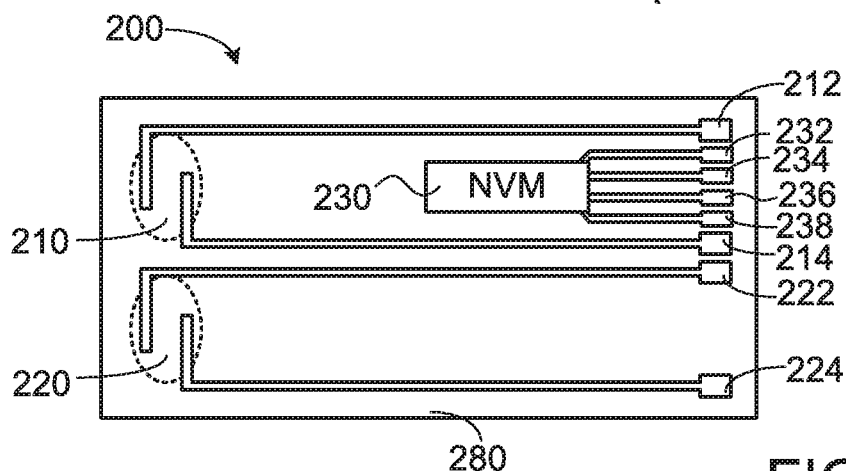

FIG. 2A

| A chemical reagent is applied on the calibration site and the test site of the blood glucose test strip | S520 |

| A calibrating procedure is performed to drop a calibration solution on the calibration site, a calibration parameter is obtained according to a reaction between the calibration solution and the chemical reagent, and the calibration parameter is stored into the non-volatile memory of the blood glucose test strip | S522 |

| A blood sample is dropped on the test site, and an output blood glucose level is calculated according to a reaction between the blood sample and the chemical reagent and the calibration parameter in the non-volatile memory | S524 |

FIG. 2B

BLOOD GLUCOSE TEST STRIP AND ASSOCIATED MEASURING METHOD

This application claims the benefit of U.S. provisional application Ser. No. 62/791,870, filed Jan. 13, 2019, and Taiwan application Serial No. 108140518, filed Nov. 7, 2019, the subject matters of which are incorporated herein by references.

FIELD OF THE INVENTION

The present invention relates to a test strip and an associated measuring method, and more particularly to a blood glucose test strip and an associated measuring method.

BACKGROUND OF THE INVENTION

For some diabetic patients, it is necessary to control blood glucose for a long time. Generally, a blood glucose meter is an indispensable tool for self-monitoring the blood glucose levels. Moreover, according to the blood glucose levels, the doctors can give individual medication advices to the diabetic patients. Consequently, the blood glucose levels can be controlled to be in a stable range.

Generally, the blood glucose meter needs to cooperate with blood glucose test strips. Firstly, the user drops the blood on the blood glucose test strip. After the blood glucose test strip is inserted into the blood glucose meter, a measuring circuit within the blood glucose meter measures the blood glucose level of the blood sample on the blood glucose test strip. In addition, the blood glucose level is shown on a display screen of the blood glucose meter. The user can realize the blood glucose level through the display screen of the blood glucose meter.

FIG. 1 schematically illustrates the structure of a conventional blood glucose test strip. As shown in FIG. 1, the blood glucose test strip 100 comprises a base substrate 180 and plural electrodes 140, 160. The base substrate 180 has a test site 120. The electrodes 140 and 160 are in contact with the test site 120. Moreover, a chemical reagent is applied on the test site 120.

When the user drops a blood sample on the test site 120 of the blood glucose test strip 100, the blood sample reacts with the chemical reagent at the test site 120, and the resistance value of the reactant changes with the blood glucose concentration in the blood sample. After the blood glucose test strip 100 is inserted into the blood glucose meter, the blood glucose level is detected by the blood glucose meter.

For example, a measuring circuit within the blood glucose meter provides a test voltage to the electrodes 140 and 160 and calculates the blood glucose level of the blood sample according to the generated current value. Alternatively, the measuring circuit within the blood glucose meter provides a test current to the electrodes 140 and 160 and calculates the blood glucose level of the blood sample according to the generated voltage value. As shown in FIG. 1, the blood glucose test strip 100 comprises two electrodes. Alternatively, the blood glucose test strip 100 comprises more than two electrodes. These electrodes are connected with the test site 120. Consequently, the blood glucose level can be detected by the measuring circuit within the blood glucose meter.

Since the concentration of the chemical reagent may be affected by environmental factors, the blood glucose level measured by the blood glucose meter may be inaccurate. During the process of manufacturing the blood glucose test strip, the manufacturer will apply the chemical reagent to all of the blood glucose test strips in one batch (for example, one batch of 1005 blood glucose test strips). Moreover, the manufacturer will take some of the blood glucose test strips (e.g., 1 to 5 blood glucose test strips) to perform a calibration procedure and obtain a calibration parameter. The remaining blood glucose test strips of the batch are corrected according to the calibration parameter. For example, when 50 blood glucose test strips of the batch are packaged and sold, the manufacturer will print out the calibration parameters of the batch of blood glucose test strips on 20 packing boxes.

After the user purchases one box of blood glucose test strips, the user can see the calibration parameter that is printed on the packing box. Before the box of blood glucose test strips are used, the user has to input the calibration parameter into the blood glucose meter. After the blood glucose test strip is inserted into the blood glucose meter, the blood glucose meter calculates the blood glucose level according to the calibration parameter.

After the box of blood glucose test strips are used up, the user has to purchase another box of blood glucose test strips. Before the box of blood glucose test strips are used, the user has to input the new calibration parameter into the blood glucose meter. After the blood glucose test strip is inserted into the blood glucose meter, the blood glucose meter calculates the blood glucose level according to the new calibration parameter.

However, if the user forgets to input the new calibration parameter into the blood glucose meter, the blood glucose level detected by the blood glucose meter according to the old calibration parameter is inaccurate.

According to the above calibrating method, the blood glucose test strips in the same batch have a shared calibration parameter. In fact, the error of the blood glucose level detected by using the conventional calibrating method is possibly 30% or higher. In other words, the conventional calibrating method may cause clinical misjudgment.

SUMMARY OF THE INVENTION

An embodiment of the present invention provides a blood glucose test strip. The blood glucose test strip includes a base substrate, a calibration site, a test site and a non-volatile memory. The calibration site is disposed on the base substrate. A chemical reagent is applied on the calibration site. The test site is disposed on the base substrate. A chemical reagent is applied on the test site. The non-volatile memory is disposed on the base substrate. A calibration parameter is stored in the non-volatile memory. During a calibrating procedure, the calibration solution is dropped on the calibration site, a calibration parameter is calculated according to a first reaction result of the calibration solution and the chemical reagent, and the calibration parameter is stored in the non-volatile memory.

Another embodiment of the present invention provides a measuring method for a blood glucose test strip. The blood glucose test strip includes a calibration site, a test site and a non-volatile memory. The measuring method includes the following steps. Firstly, a chemical reagent is applied on the calibration site and the test site of the blood glucose test strip. Then, a calibration solution is dropped on the calibration site, a calibration parameter is calculated according to a first reaction result of the calibration solution and the chemical reagent, and the calibration parameter is stored into the non-volatile memory of the blood glucose test strip. Then, a blood sample is dropped on the test site, and an output blood glucose level is calculated according to a second reaction result of the blood sample and the chemical reagent and the calibration parameter in the non-volatile memory.

Numerous objects, features and advantages of the present invention will be readily apparent upon a reading of the following detailed description of embodiments of the present invention when taken in conjunction with the accompanying drawings. However, the drawings employed herein are for the purpose of descriptions and should not be regarded as limiting.

BRIEF DESCRIPTION OF THE DRAWINGS

The above objects and advantages of the present invention will become more readily apparent to those ordinarily skilled in the art after reviewing the following detailed description and accompanying drawings, in which:

FIG. 1 (prior art) schematically illustrates the structure of a conventional blood glucose test strip;

FIG. 2A schematically illustrates the structure of a blood glucose test strip according to a first embodiment of the present invention;

FIG. 2B is a flowchart illustrating a measuring method for a blood glucose test strip according to an embodiment of the present invention;

DETAILED DESCRIPTION OF PREFERRED EMBODIMENTS

Figure 3:
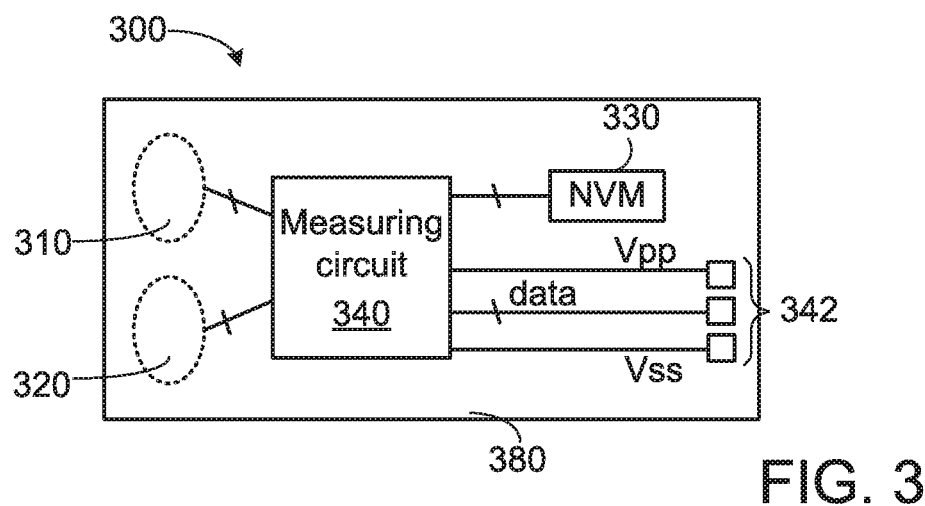
FIG. 3 schematically illustrates the structure of a blood glucose test strip according to a second embodiment of the present invention.

FIG. 2A schematically illustrates the structure of a blood glucose test strip according to a first embodiment of the present invention. As shown in FIG. 2A, the blood glucose test strip 200 comprises a base substrate 280, a calibration site 210, a test site 220, a non-volatile memory (NVM) 230 and plural electrodes 212, 214, 222, 224, 232, 234, 236 and 238. The calibration site 210 and the test site 220 are disposed on the base substrate 280. The electrodes 212 and 214 are contacted with the calibration site 210. The electrodes 222 and 224 are contacted with the test site 220. The electrodes 232, 234, 236 and 238 are contacted with the non-volatile memory 230.

During the process of manufacturing the blood glucose test strip 200, a chemical reagent is applied on the calibration site 210 and the test site 220. In a calibrating procedure, a calibration solution is dropped on the calibration site 210. The blood glucose concentration of the calibration solution is known. After the calibration solution reacts with the chemical reagent, a calibration circuit (not shown) is connected with the electrodes 212 and 214 to obtain a specified value and calculates a calibration parameter of the blood glucose test strip 200 according to the specified value. Moreover, the calibration parameter is transmitted from the calibration circuit (not shown) to the non-volatile memory 230 through the electrodes 232, 234, 236 and 238 and stored into the non-volatile memory 230. In other words, each blood glucose test strip 200 is subjected to the calibrating procedure by the manufacturer. In addition, the non-volatile memory 230 of each blood glucose test strip 200 stores the corresponding calibration parameter.

After the blood sample of the user is dropped on the test site 220 of the blood glucose test strip 200, the blood sample reacts with the chemical reagent on the test site 220. The resistance value of the reactant changes with the blood glucose level. Then, the blood glucose test strip 200 is inserted into the blood glucose meter.

For example, a measuring circuit within the blood glucose meter provides a test voltage to the electrodes 222 and 224 and calculates the blood glucose level of the blood according to the generated current value. Alternatively, the measuring circuit within the blood glucose meter provides a test current to the electrodes 222 and 224 and calculates the blood glucose level of the blood according to the generated voltage value.

Moreover, the measuring circuit within the blood glucose meter reads the stored calibration parameter from the non-volatile memory 230 through the electrodes 232, 234, 236 and 238 and converts the estimated blood glucose level into the output blood glucose level. In addition, the output blood glucose level is shown on a display screen of the blood glucose meter.

FIG. 2B is a flowchart illustrating a measuring method for a blood glucose test strip according to an embodiment of the present invention. Firstly, a chemical reagent is applied on the calibration site 210 and the test site 220 of the blood glucose test strip 200 (Step S520). Then, a calibrating procedure is performed to drop a calibration solution on the calibration site 210, a calibration parameter is obtained according to a reaction between the calibration solution and the chemical reagent, and the calibration parameter is stored into the non-volatile memory 230 of the blood glucose test strip 200 (Step S522). Then, a blood sample is dropped on the test site 220, and an output blood glucose level is calculated according to a reaction between the blood sample and the chemical reagent and the calibration parameter in the non-volatile memory 230 (Step S524).

Since the blood glucose test strip 200 is equipped with the non-volatile memory 230 to store the calibration parameter of the blood glucose test strip 200, the output blood glucose level calculated by the blood glucose meter is more accurate.

In this embodiment, the two electrodes 212 and 214 of the blood glucose test strip 200 are connected with the calibration site 210, and the two electrodes 222 and 224 of the blood glucose test strip 200 are connected with the test site 220. It is noted that numerous modifications and alterations may be made while retaining the teachings of the invention. For example, in another embodiment, more electrodes are connected with the calibration site 210 and the test site 220.

Especially, the user can perform the calibrating procedure on the blood glucose test strip 200. For example, when the manufacturer sells the blood glucose test strip 200, the calibration solution is attached. Consequently, the calibrating procedure can be performed by the user. After the user drops the calibration solution on the calibration site 210 and the blood glucose test strip 200 is inserted into the blood glucose meter, the calibration parameter is calculated by the blood glucose meter and the calibration parameters are stored in the non-volatile memory 230 of the blood glucose test strip 200. For measuring the blood glucose level of the user, the user drops the blood sample on the test site 220. According to the reaction between the blood sample and the chemical reagent and the calibration parameter in the non-volatile memory 230, the output blood glucose level is calculated by the measuring circuit within the blood glucose meter.

In an embodiment, the measuring circuit is installed in the blood glucose test strip, and the blood glucose level is shown on an ordinary electronic device. FIG. 3 schematically illustrates the structure of a blood glucose test strip according to a second embodiment of the present invention. As shown in FIG. 3, the blood glucose test strip 300 comprises a base substrate 380, a calibration site 310, a test site 320, a non-volatile memory 330, a measuring circuit 340 and a communication port 342. The calibration site 310 and the test site 320 are disposed on the base substrate 380. A chemical reagent is applied on the calibration site 310 and the test site 320 of the blood glucose test strip 300. The communication port 342 of the blood glucose test strip 300 is connected with an electronic device (not shown). For example, the communication port 342 is a USB port.

Moreover, plural first conductor lines are connected between the measuring circuit 340 and the calibration site 310, plural second conductor lines are connected between the measuring circuit 340 and the test site 320, and plural third conductor lines are connected between the measuring circuit 340 and the non-volatile memory 330. Moreover, the measuring circuit 340 has the communication port 342.

After the blood glucose test strip 300 is inserted into the electronic device with the same communication port 342, the measuring circuit 340 of the blood glucose test strip 300 receives the power voltages Vpp and Vss from the electronic device. Meanwhile, the user or the manufacturer can perform the calibrating procedure. An example of the electronic device is a computer or a smart phone.

In a calibrating procedure, the user or the manufacturer drops the calibration solution on the calibration site 310. The blood glucose concentration of the calibration solution is known. After the calibration solution reacts with the chemical reagent, the measuring circuit 340 calculates the calibration parameter of the blood glucose test strip 300. Moreover, the calibration parameter is transmitted from the measuring circuit 340 to the non-volatile memory 330 and stored into the non-volatile memory 330. In other words, the calibrating procedure can be performed by the user or the manufacturer. In addition, the non-volatile memory 330 of each blood glucose test strip 300 stores the corresponding calibration parameter.

Similarly, after the blood sample is dropped on the test site 320 of the blood glucose test strip 300, the blood glucose test strip 300 is inserted into the electronic device with the same communication port 342. Since the measuring circuit 340 of the blood glucose test strip 300 receives the power voltages Vpp and Vss from the electronic device, the blood glucose test strip 300 is in the normal working state. Meanwhile, the user can measure the blood glucose level.

After the blood sample of the user is dropped on the test site 320 of the blood glucose test strip 300, the blood sample reacts with the chemical reagent on the test site 320. Consequently, the estimated blood glucose level is measured by the measuring circuit 340. Moreover, the measuring circuit 340 reads the stored calibration parameter from the non-volatile memory 330 and converts the estimated blood glucose level into the output blood glucose level. Then, the output blood glucose level is transmitted from the measuring circuit 340 to the electronic device through a data line (data) of the communication port 342. Consequently, the output blood glucose level is shown on a display screen of the electronic device.

The measuring method as shown in FIG. 2B is also applied to the blood glucose test strip 300 of this embodiment. The detailed flowchart is not redundantly described herein.

As mentioned above, the blood glucose test strip 300 of this embodiment comprises the measuring circuit 340, and the calibration parameter is stored in the non-volatile memory 330. Consequently, the blood glucose test strip 300 can be subjected to the calibrating procedure and used to measure the blood glucose level. Since the blood glucose test strip 300 comprises the communication port 342, the output blood glucose level calculated by the measuring circuit 340 can be transmitted to the electronic device through the communication port 342. In such way, the output blood glucose level is shown on the display screen of the electronic device.

Figure 4:
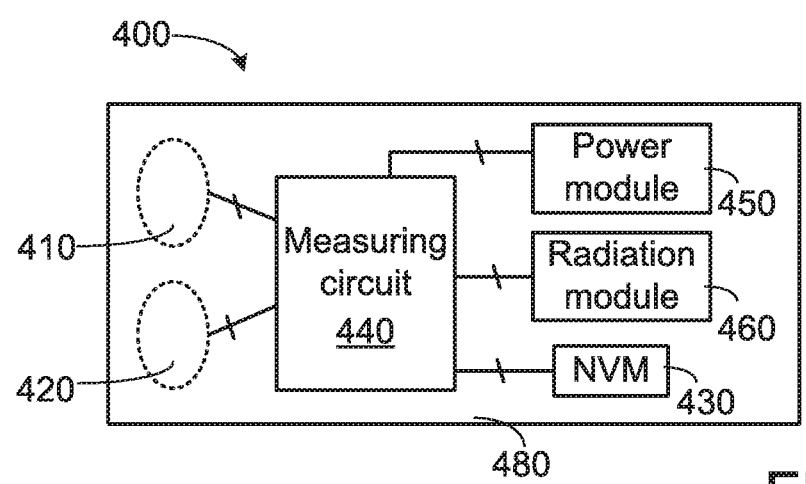
FIG. 4 schematically illustrates the structure of a blood glucose test strip according to a third embodiment of the present invention.

In another embodiment, the output blood glucose level can be transmitted from the blood glucose test strip to the electronic device in a wireless transmission manner. FIG. 4 schematically illustrates the structure of a blood glucose test strip according to a third embodiment of the present invention. As shown in FIG. 4, the blood glucose test strip 400 comprises a base substrate 480, a calibration site 410, a test site 420, a non-volatile memory 430, a measuring circuit 440, a power module 450 and a radiation module 460. The calibration site 410 and the test site 420 are disposed on the base substrate 480. A chemical reagent is applied on the calibration site 410 and the test site 420 of the blood glucose test strip 400. The power module 450 of the blood glucose test strip 400 provides electric power to the measuring circuit 440. The output blood glucose level is transmitted from the radiation module 460 to the external electronic device according to a wireless transmission technology.

The measuring circuit 440 is connected with the calibration site 410, the test site 420, the non-volatile memory 430, the power module 450 and the radiation module 460. The power module 450 is an induction coil module. The radiation module 460 is a Bluetooth module, a WiFi module, a RF module or a NFC module.

When the power module 450 of the blood glucose test strip 400 provides electric power to the measuring circuit 440, the measuring circuit 440 is in the normal working state. Meanwhile, the user or the manufacturer can perform the calibrating procedure.

When the blood glucose test strip 400 is close to a near-field communication (NFC) electronic device, the power module 450 of the blood glucose test strip 400 induces the electric power and provides the electric power to the measuring circuit 440. It is noted that the example of the power module 450 is not restricted. For example, in another embodiment, the power module 450 is a battery module.

In a calibrating procedure, the user or the manufacturer drops the calibration solution on the calibration site 410. The blood glucose concentration of the calibration solution is known. After the calibration solution reacts with the chemical reagent, the measuring circuit 440 calculates the calibration parameter of the blood glucose test strip 400. Moreover, the calibration parameter is transmitted from the measuring circuit 440 to the non-volatile memory 430 and stored into the non-volatile memory 430. In other words, the calibrating procedure can be performed by the user or the manufacturer. In addition, the non-volatile memory 430 of each blood glucose test strip 400 stores the corresponding calibration parameter.

Similarly, the blood glucose test strip 400 can be used to measure the blood glucose level. After the blood sample is dropped on the test site 420 of the blood glucose test strip 400, the blood sample reacts with the chemical reagent on the test site 420. Consequently, the estimated blood glucose level is measured by the measuring circuit 440. Moreover, the measuring circuit 440 converts the estimated blood glucose level into the output blood glucose level according to the calibration parameter in the non-volatile memory 430.

Then, the output blood glucose level is transmitted from the measuring circuit 440 to the electronic device (not shown) through the radiation module 460. Consequently, the output blood glucose level is shown on a display screen of the electronic device.

The measuring method as shown in FIG. 2B is also applied to the blood glucose test strip 400 of this embodiment. The detailed flowchart is not redundantly described herein.

As mentioned above, the blood glucose test strip 400 of this embodiment comprises the measuring circuit 440, and the calibration parameter is stored in the non-volatile memory 430. Consequently, the blood glucose test strip 400 can be subjected to the calibrating procedure and used to measure the blood glucose level. Since the blood glucose test strip 400 comprises the radiation module 460, the output blood glucose level calculated by the measuring circuit 440 can be transmitted to the electronic device according to the wireless transmission technology. In such way, the output blood glucose level is shown on the display screen of the electronic device.

From the above description, the present invention provides a blood glucose test strip with electronic components. Each blood glucose test strip undergoes the calibrating procedure. The calibration parameter is stored in the non-volatile memory. Consequently, the accuracy of measuring the blood glucose level is largely enhanced. Since the blood glucose test strip 400 has the electronic structure, the user does not need to carry the conventional blood glucose meter. Consequently, the blood glucose test strip of the present invention is user-friendly.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A blood glucose test strip, comprising:
   a base substrate;
   a calibration site disposed on the base substrate, wherein a chemical reagent is applied on the calibration site;
   a first set of electrodes contacted with the calibration site;
   a test site disposed on the base substrate, wherein a chemical reagent is applied on the test site;
   a second set of electrodes contacted with the test site;
   a non-volatile memory disposed on the base substrate, wherein a calibration parameter is stored in the non-volatile memory; and
   a third set of electrodes contacted with the non-volatile memory;
   wherein during a calibrating procedure, a calibration solution is dropped on the calibration site, a calibration circuit is connected with the first set of electrode and the third set of electrodes, the calibration parameter is calculated by the calibration circuit according to a first reaction result of the calibration solution and the chemical reagent, and the calibration parameter is transmitted from the calibration circuit to the non-volatile memory through the third set of electrodes and stored in the non-volatile memory.

2. The blood glucose test strip as claimed in claim 1, wherein after a blood sample is dropped on the test site, an output blood glucose level is calculated by a measuring circuit of a blood glucose meter according to a second reaction result of the blood sample and the chemical reagent and the calibration parameter.

3. The blood glucose test strip as claimed in claim 1, wherein the blood glucose test strip further comprises a measuring circuit, wherein the measuring circuit is disposed on the base substrate, and the measuring circuit is connected with the calibration site, the test site and the non-volatile memory, wherein during the calibrating procedure, the measuring circuit calculates the calibration parameter according to the first reaction result of the calibration solution and the chemical reagent and stores the calibration parameter in the non-volatile memory.

4. The blood glucose test strip as claimed in claim 3, wherein after the blood sample is dropped on the test site, the measuring circuit calculates the output blood glucose level according to a second reaction result of the blood sample and the chemical reagent and the calibration parameter.

5. The blood glucose test strip as claimed in claim 4, wherein the measuring circuit comprises a communication port, and the communication port is connected with an electronic device, wherein the output blood glucose level is transmitted from the measuring circuit to the electronic device through the communication port, and the output blood glucose level is shown on a display screen of the electronic device.

6. The blood glucose test strip as claimed in claim 5, wherein the electronic device provides electric power to the measuring circuit through the communication port, so that the measuring circuit is in a normal working state.

7. The blood glucose test strip as claimed in claim 4, wherein the blood glucose test strip further comprises a power module and a radiation module, which are disposed on the base substrate, wherein the measuring circuit is connected with the power module and the radiation module, and the power module provides electric power to the measuring circuit, so that the measuring circuit is in a normal working state.

8. The blood glucose test strip as claimed in claim 7, wherein the output blood glucose level is transmitted from the measuring circuit to the electronic device through the radiation module, and the output blood glucose level is shown on a display screen of the electronic device.

9. A measuring method for a blood glucose test strip, the blood glucose test strip comprising a calibration site, a test site and a non-volatile memory, the measuring method comprising steps of:
   applying a chemical reagent on the calibration site and the test site of the blood glucose test strip;
   dropping a calibration solution on the calibration site, calculating a calibration parameter according to a first reaction result of the calibration solution and the chemical reagent, and storing the calibration parameter into the non-volatile memory of the blood glucose test strip; and
   dropping a blood sample on the test site, and calculating an output blood glucose level according to a second reaction result of the blood sample and the chemical reagent and the calibration parameter in the non-volatile memory.

10. The measuring method as claimed in claim 9, wherein the blood glucose test strip further comprises a measuring circuit, wherein the measuring circuit calculates the calibration parameter according to the first reaction result and stores the calibration parameter in the non-volatile memory, and the measuring circuit calculates the output blood glucose level according to the second reaction result and the calibration parameter in the non-volatile memory.

11. The measuring method as claimed in claim 10, further comprising steps of: connecting a communication port of the measuring circuit with an electronic device, and transmitting the output blood glucose level from the measuring circuit to the electronic device through the communication port, so that the output blood glucose level is shown on a display screen of the electronic device.

12. The measuring method as claimed in claim 10, wherein the blood glucose test strip further comprises a power module and a radiation module, which are connected with the measuring circuit, wherein the power module provides electric power to the measuring circuit, so that the measuring circuit is in a normal working state.

13. The measuring method as claimed in claim 12, further comprising a step of transmitting the output blood glucose level from the measuring circuit to the electronic device through the radiation module, so that the output blood glucose level is shown on a display screen of the electronic device.

\* \* \* \* \*